United States Patent
Baum et al.

(10) Patent No.: US 8,690,759 B2
(45) Date of Patent: Apr. 8, 2014

(54) ENDOSCOPIC INSTRUMENT

(75) Inventors: Eckhart Baum, Duerbheim (DE); Peter Schwarz, Tuttlingen-Nendingen (DE)

(73) Assignee: Karl Storz GmbH & Co. KG (DE)

( * ) Notice: Subject to any disclaimer, the term of this patent is extended or adjusted under 35 U.S.C. 154(b) by 160 days.

(21) Appl. No.: 13/184,052

(22) Filed: Jul. 15, 2011

(65) Prior Publication Data

US 2012/0016202 A1    Jan. 19, 2012

(30) Foreign Application Priority Data

Jul. 15, 2010  (DE) .......................... 10 2010 027 400

(51) Int. Cl.
*A61B 1/00* (2006.01)
*A61B 1/04* (2006.01)

(52) U.S. Cl.
USPC ........................................ 600/110; 600/128

(58) Field of Classification Search
USPC ................. 600/109, 110, 111, 128, 132, 175
See application file for complete search history.

(56) References Cited

U.S. PATENT DOCUMENTS

| | | | | |
|---|---|---|---|---|
| 2,081,427 A * | 5/1937 | Firth et al. | ...................... | 174/34 |
| 5,058,568 A | 10/1991 | Irion et al. | | |
| 5,976,070 A * | 11/1999 | Ono et al. | ...................... | 600/110 |
| 6,007,480 A | 12/1999 | Iida et al. | | |
| 7,773,122 B2 * | 8/2010 | Irion et al. | ................. | 348/222.1 |
| 7,899,948 B2 | 3/2011 | Olschner et al. | | |
| 2002/0028982 A1 * | 3/2002 | Takahashi | ..................... | 600/110 |
| 2002/0036096 A1 * | 3/2002 | Groegl et al. | ............. | 174/106 R |
| 2003/0141098 A1 * | 7/2003 | Grogl et al. | ............... | 174/110 R |
| 2004/0157493 A1 * | 8/2004 | Bergner et al. | ............... | 439/610 |
| 2004/0176661 A1 * | 9/2004 | Futatsugi | ..................... | 600/110 |
| 2004/0197058 A1 | 10/2004 | Eichelberger et al. | | |
| 2005/0014996 A1 * | 1/2005 | Konomura et al. | ........... | 600/175 |
| 2005/0029006 A1 | 2/2005 | Takahashi et al. | | |
| 2006/0114986 A1 * | 6/2006 | Knapp et al. | ............. | 375/240.01 |
| 2008/0136903 A1 * | 6/2008 | Takada et al. | ................... | 348/65 |
| 2009/0306475 A1 * | 12/2009 | Yamamoto et al. | ........... | 600/110 |
| 2010/0261961 A1 | 10/2010 | Scott et al. | | |

FOREIGN PATENT DOCUMENTS

| | | |
|---|---|---|
| DE | 3817915 A1 | 11/1989 |
| DE | 19735989 A1 | 2/1998 |
| DE | 102007038725 B3 | 2/2009 |
| EP | 0819311 B1 | 1/1998 |
| EP | 0946951 B1 | 10/1999 |
| JP | 2005160925 A | 6/2005 |

* cited by examiner

*Primary Examiner* — Philip R Smith
(74) *Attorney, Agent, or Firm* — St. Onge Steward Johnston & Reens LLC (57) ABSTRACT

There is disclosed an endoscopic instrument comprising a shaft having a distal end at which at least one optical sensor is arranged and a proximal end configured for a connection to a supply unit, further comprising a data transmission element which is provided between the at least one optical sensor and the proximal end and which is configured to differentially transmit at least two signals. The data transmission element is embodied as a star quad cable.

19 Claims, 10 Drawing Sheets

ENDOSCOPIC INSTRUMENT

CROSS REFERENCES TO RELATED APPLICATIONS

This application claims priority from German patent application DE 10 2010 027 400.3, filed on Jul. 15, 2010. The entire contents of this priority application is incorporated herein by reference.

BACKGROUND OF THE INVENTION

Endoscopic optical and optoelectronic sensors comprise CCD (Charge-Coupled Device)—or CMOS (Complementary Metal Oxide Semiconductor)—modules. The requirements regarding the restricted dimensions of endoscopic instruments can make it difficult to provide the image data processing units and control units for these sensors at the distal end of the endoscopic instrument. Therefore, data transmission elements are provided which transmit the image data from the optical sensors to a supply unit and vice versa transmit control signals and driving clock cycles from the supply unit to the optical sensor.

For the data transmission of analog video signals and driver clocks having a relatively high frequency, coaxial conductors with a length of several meters have been typically used. The use of coaxial conductors is common for frequencies of more than one Megahertz (MHz), since they provide a low signal attenuation and are typically free of crosstalk at high frequencies. The data transmission systems for endoscopic optical sensors, i.e. camera or video modules, which transmit image data in a PAL- or NTSC-standard format, typically comprise a plurality of coaxial conductors for the image data and the driver clocks at a high frequency and further single elements for a voltage supply, a shutter signal or driver clocks at a low frequency.

Examples for endoscopic systems are shown in documents U.S. Pat. No. 6,007,480 and U.S. Pat. No. 5,058,568.

In the field of endoscopic optical sensors the demands regarding image quality and image resolution have continuously increased. In the same manner the bandwidth required for the required transmission of digital data increases. Parallel interfaces are difficult to implement, since they require many connections and have a rather high power demand. The available space and power consumption, however, are typically parameters that may be critical in endoscopic applications and should be kept small. Therefore, there is a demand for serial interfaces having a wide bandwidth for the transmission of analog and digital data.

It has been suggested for new endoscopic optical sensors to convert the image data signal of the optical sensor into a differential serial LVDS (Low Voltage Differential Signaling)-Signal in order to use this interface standard for transmitting image data at high speeds. Converting the image data, however, requires a further converter element which itself requires a certain space. Twisted pair cables are used as data transmission elements. Twisted pair cables are cables that have twisted pairs of strands. The twisted pairs of strands are provided with symmetrical signals in order to evaluate a difference between the signals on both strands at the proximal end of the data transmission element, e.g. using differential amplifier. Typically, the signal applied at the distal end may thus be reconstructed in an optimal manner at the proximal side of the receiver.

Examples for twisted pair cables can be found, e.g., in documents EP 0 819 311 B1 and EP 0 946 951 B1.

However, twisted pair cables have a relatively large diameter due to the twisting of the strands in order to have a sufficiently low signal attenuation considering the required length of the cable and the transmission bandwidth. This would lead to an increased diameter of the endoscopic instrument, even though the diameter should be as small as possible when using the endoscopic instrument in a procedure involving a human being.

Optical sensors having a high resolution are increasingly available in large numbers for consumers, in particular in the field of telecommunications. These sensors are used, e.g., in cellular telephones or digital cameras. These optical sensors may use the so-called MIPI CSI-2 (Camera Serial Interface)-standard in an increasing manner. An example is provided in document U.S. Pat. No. 7,899,948.

The MIPI CSI-2-standard defines a serial, fast and cost efficient interface between a peripheral image module and a mobile device with small dimensions. In particular, it is embodied as a serial interface having a high bandwidth for the transmission of image and video data over small distances of less than 30 cm (approx. 11.8 in) within a mobile consumer device.

Using miniaturized CMOS-sensors that are designed and available in large numbers for the field of telecommunications can be interesting also in the field of endoscopic instruments. Today, proprietary solutions are developed which come at a significant cost. When using the image sensors that are known from telecommunications, it would be necessary to use the MIPI CSI-2 interface as well. In order to provide the data transmission, solutions in the field of communications use flexible printed circuit boards or the previously mentioned twisted pair cables, which does not pose notable problems due to the short cable lengths in cellular devices and the resulting attenuation.

In endoscopic applications the transmission paths are typically much longer, necessitating larger diameters of cables in order to maintain a small attenuation. However, the increased diameter may not to be acceptable for the field of endoscopy. If a solution to this problem could be found, significant economic advantages could be achieved and the quality of the image transmission could be significantly increased.

It is an object of the present invention to provide an improved endoscopic instrument. It is a further object of the present invention to provide a solution for using the image sensors known from the field of telecommunications and their digital signal interfaces also in the field of endoscopy while considering the required dimensions of the instruments and the diameters of the cables.

SUMMARY OF THE INVENTION

According to the invention there is provided an endoscopic instrument, wherein the data transmission element is embodied as a star quad cable.

Using a star quad cable as a data transmission element allows, e.g., to use CMOS or CCD sensors with HD resolutions of 1920×1080 pixels, since it is possible to use data rates of over 400 Mbit/sec with a small diameter cable and a corresponding small space at the distal end. The star quad cable may provide a small cable diameter and a small attenuation at the same time. Due to the differential signal transmission a low noise signal reconstruction at the proximal end or at the supply unit may be possible, even though a very small diameter for the conductor is used.

In the applicable frequency range the dampening of a cable is predominantly dependent on the skin effect known to the skilled person. The losses caused by the skin effect increase when the signal frequency increases (meaning with an increasing bit rate) and as the cable diameter gets smaller. In order to achieve frame rates of about 30 images per second at high resolution data rates of more than 400 Mbit/sec, in particular up to 960 Mbit/sec, are required. A data transmission element that is suitable for the transmission of such bit rates over a given length, meaning from the distal end at least to the proximal end, must have at least a minimum diameter, depending on its particular construction, in order to take into account the skin effect.

Using a data transmission element having a star quad arrangement, in particular embodied as a symmetric arrangement, may resolve the conflict present in endoscopic applications between the small outer dimensions and the high transmission quality and transmission bandwidth. A star quad cable arrangement may offer a compact structure in comparison to other data transmission elements and may offer a smaller attenuation when comparing same diameters. It is therefore possible to provide a good transmission quality at high resolutions of 1920×1080 pixels and a corresponding frame rate (30/60 Hz) also for endoscopic applications at the required smallest diameters.

The individual transmission pairs or strand pairs of the star quad arrangement do not require a shielding, since a potential cross talk always applies to both strands of the other pair of strands and is thus cancelled at the corresponding differential receiver. In the context of this application, the term "strand" in the context of "strand pair", "strand pairs", "pair of strands" or "pairs of strands" can refer to an electrically conducting strand of wire as well as to an optical strand, however, the understanding of electrical strand is used in the context of the preferred embodiments.

The term "endoscopic instrument" relates in particular to all possible endoscopic medical instruments, which are inserted into the body of a patient and which comprise an optical sensor at the distal end. In particular it relates to an endoscope or a catheter. It can, however, also relate to an endoscopic instrument in any other application, in particular in technical fields where the available space is a critical parameter.

In general, the term "supply unit" of the endoscopic instruments relates to a device arrangement at the proximal end which is provided and required in order to operate the endoscopic instrument. The supply unit can, e.g., provide the voltage for the endoscopic instrument, can provide a connection to light-guiding cables or provide air and pneumatic pressure or can operate a suction unit that may be present in the endoscopic instrument. The supply unit may comprise an image processing unit for processing the image data that is provided by the at least one optical sensor and may comprise a display unit for displaying image data. The supply unit may also comprise operating elements that are required to operate the endoscopic instrument.

The optical sensor may be a camera, which is suitable for single frame recordings and/or video recordings.

According to a further aspect of the present invention the use of a star quad cable for data transmission to and/or from at least one optical sensor in an endoscopic instrument also provides the advantages explained in the context of the endoscopic instrument above.

According to a refinement of the invention it may be advantageous, if only two differential signals are to be transmitted, that the first signal is an image data signal and a second signal is a clock signal. Preferably, the first signal and the second signal are transmitted differentially.

According to a further refinement of the invention the at least one optical sensor is connected to the star quad cable, such that at least three signals can be transmitted differentially.

This allows to operate a second optical sensor. Two data transmission channels are provided to transmit the image information from the two sensors separately. A further data channel is provided in order to transmit a clock signal which may be identical for both optical sensors. In this manner, e.g., a stereoscopic video system may be provided at the distal end.

Alternatively, for an arrangement having one optical sensor the image data signal can be separated into two channels. Since the transmission bandwidth per channel is reduced, the data may be transmitted over longer distances with a good signal quality at high resolution.

According to a further refinement of the invention the at least one optical sensor is connected to the star quad cable, such that four signals can be transmitted differentially.

It is thus possible to transmit two separate image data signals and two separate clock signals. This allows, e.g., to use two optical sensors which do not necessarily rely on the same clock signal. It is thus possible to provide a stereo system or stereo endoscope. Also, a fluorescence endoscope may be provided.

In particular, a first and a second optical sensor may be provided, wherein a first signal is an image data signal and a second signal is a clock signal of the first optical sensor, and wherein a third signal is an image data signal and a fourth signal is a clock signal of the second optical sensor. Preferably, the first, the second, the third and the fourth signal may be transmitted differentially.

This allows to increase the overall length of the conductor while maintaining, e.g., the same transmission quality and the same outer diameter of the star quad cable.

According to a further refinement of the invention the star quad cable comprises at least a first pair of strands having two strands arranged in opposition to each other, in particular in relation to a center of the data transmission element in its longitudinal direction, and a second pair of strands having two strands in opposition to each other, in particular in relation to a center of the data transmission element, wherein the strands of the first pair of strands have a diameter different from the diameter of the strands of the second pair of strands.

In particular, the pair of strands that is provided to transmit the image data, may have a larger diameter than the other pair of strands that is provided to transmit the clock signal.

Since the transmission of the image data typically has higher requirements regarding the transmission quality, it is therefore possible to provide a good transmission quality of the image data by maintaining the same outer diameter of the data transmission element.

According to a further refinement of the invention the star quad cable comprises at least a first pair of strands having two strands in opposition to each other and a second pair of strands having two strands in opposition to each other, wherein in the clearance between the first pair of strands and the second pair of strands at least one additional strand is arranged.

In the context of this application it is noted, that the term "additional strand" may refer to an electrical strand or a wire as well as an optical strand or an optical fiber.

The additional strand is preferably arranged in the center of the data transmission element and is preferably embodied as a ground wire. Alternatively or in addition it is preferred to arrange an additional strand or additional strands in such a manner that the center of such additional strand is provided at a greater radial distance to the center of the data transmission element than the radial distance of the centers of the strands of the strand pairs to the center of the data transmission element.

Preferably, the largest radial distance of such an additional strand—when considering the cross section of the strand—to the center of the data transmission element is less or equal to the largest radial distance of the strands of the pairs of strands—when considering the cross section of the strands. This eliminates the need for an increased outer diameter, even though additional strands are provided.

According to a further refinement of the invention, the at least one additional strand is provided for a power supply of the at least one optical sensor or for the control of the at least one optical sensor or is embodied as an optical fiber.

This allows to integrate further conductors, e.g. for supplying power or for controlling the image sensor, into the data transmission element while maintaining the outer diameter of the data transmission element.

This may bring the advantage that in addition to the transmission of data from and to the at least one optical sensor, a transmission of light from the proximal end, e.g. from the supply unit, to the distal end is possible without increasing the outer diameter of the data transmission element. If a proximal light source uses a so-called white light laser (RGB), it is possible to use thin optical strands with an outer diameter of about 0.4 mm (approx. 0.015 in) down to about 0.125 mm (approx. 0.005 in).

According to a further refinement of the present invention a first signal is provided for transmitting image data and a second signal is provided to transmit a clock signal. In particular, the first and the second signal may be transmitted differentially.

According to a further refinement of the present invention the endoscopic instrument comprises a first and a second optical sensor, wherein a first differential signal is provided for the transmission of first image data and a second differential signal is provided for the transmission of a first clock signal of the first optical sensor, and wherein a third differential signal is provided for the transmission of second image data and a fourth differential signal is provided for the transmission of a second clock signal of the second optical sensor.

According to a further refinement of the present invention the transmission of the image data is performed using the MIPI CSI-2 standard.

The transmission according to this standard allows the utilization of standardized optical sensors and corresponding receiving modules from the end consumer market in the field of telecommunications and results in a cost-efficient manufacturing of the endoscopic instruments.

In particular, in connection with the transmission of three differential signals, there is the opportunity to use the MIPI CSI-2 "two lane" standard. When using four differential signals, two optical sensors may be operated using the MIPI CSI-2 "one lane" standard.

According to a further refinement of the invention, there is provided at the distal end a driver unit with pre-emphasis for a pre-distortion of the image data of the at least one optical sensor.

An amplification and pre-distortion at the distal end may allow a further increase of the cable length while keeping the quality of the transmission and the outer diameter essentially the same.

According to a further refinement of the invention there is provided an equalization unit at the proximal end for equalizing the image data of the at least one optical sensor. The equalization unit can be provided alternatively or in addition to the driver unit with pre-emphasis.

Based on a given outer diameter of the data transmission element an even greater cable length may become possible at essentially the same transmission quality. In particular, the equalization unit may preferably be a part of the supply unit.

According to a further refinement of the present invention the star quad cable has a diameter of less than 5 mm (approx. 0.2 in), preferably less than 4 mm (approx. 0.16 in), even more preferred less than 3 mm (approx. 0.12 in) and has a length of at least 0.5 m (approx. 1.6 ft), preferably at least 1.0 in (approx. 3.3 ft), even more preferred at least 1.5 m (approx. 4.9 ft). At the same time, the data transmission element allows for a transmission rate of at least 400 Mbit/sec, preferably at least 800 Mbit/sec, even more preferred of 960 Mbit/sec.

According to a further refinement of the invention an optical unit is associated with the at least one optical sensor, the unit being arranged at the distal end in the optical path before the optical sensor. A further refinement of the invention provides that the optical unit is equipped on one side with a connector unit which allows that the optical unit can be releasably attached distally before the at least one optical sensor and may thus be at least temporarily held in engagement with the optical sensor.

The optical unit or the releasable part of the optical unit may comprise a beam splitter, a filter, at least one lens, in particular a rod lens, a prism, a lens system or an endoscopic instrument. If more than one optical sensor is provided, an optical unit may be provided for each of the optical sensors, however, the optical unit may also be provided for a plurality or for all optical sensors.

Further advantages and refinements become apparent from the drawings and the following description of the preferred embodiments.

Various modifications to these embodiments will be readily apparent to those skilled in the art, and the generic principles defined herein may be applied to other embodiments. Thus, the description is not intended to be limited to the embodiments shown herein but is to be accorded the widest scope consistent with the principles and novel features disclosed herein.

To the accomplishment of the foregoing and related ends, the one or more embodiments comprise the features hereinafter fully described and particularly pointed out in the claims. The following description and the annexed drawings set forth in detail certain illustrative embodiments of the one or more embodiments. These embodiments are indicative, however, of but a few of the various ways in which the principles of various embodiments may be employed and the described embodiments are intended to include all such embodiments and there equivalence.

Preferred embodiments of the inventions are shown in the drawings and will be explained in the following description.

DESCRIPTION OF PREFERRED EMBODIMENTS

Figure 1:
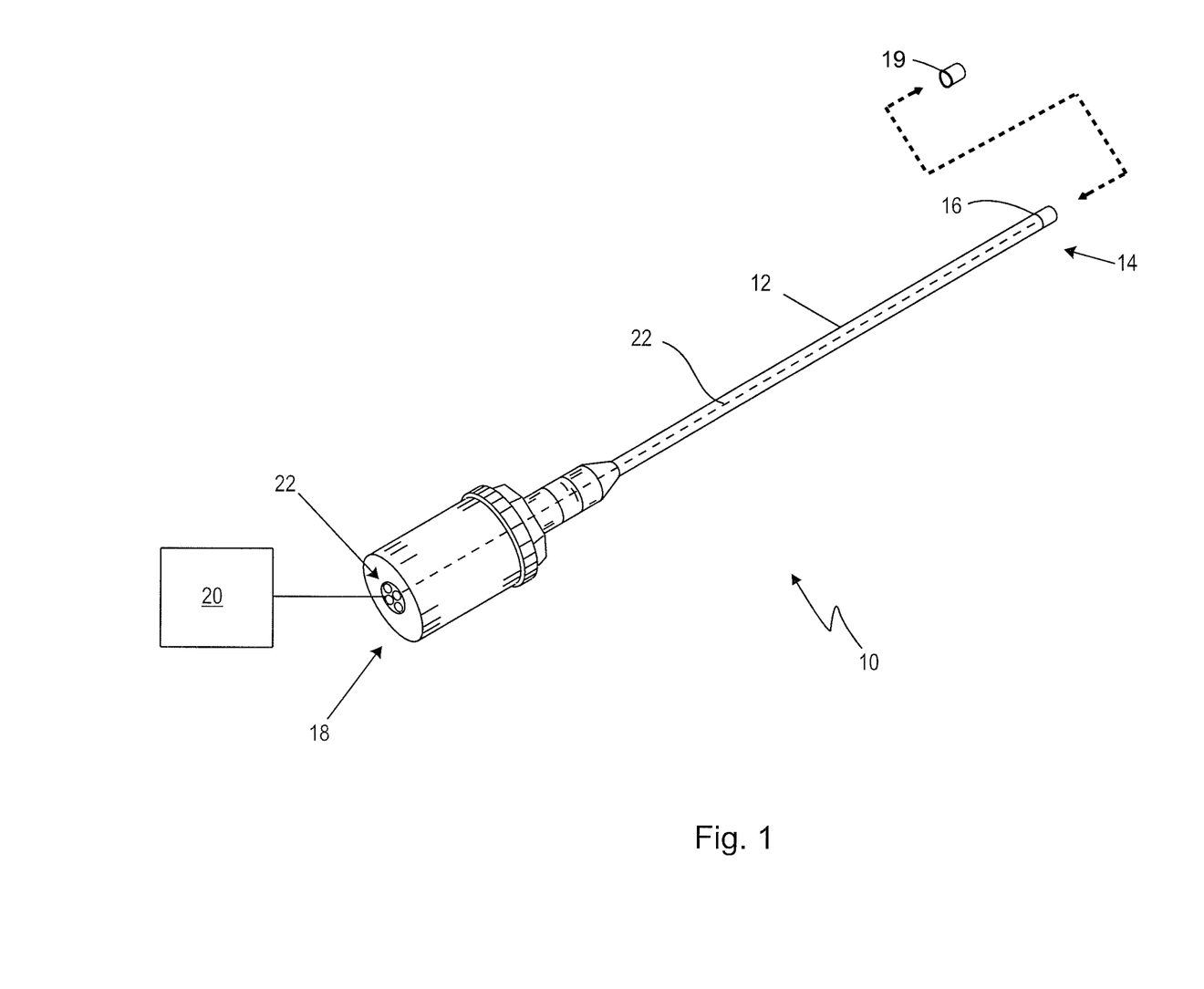
FIG. 1 illustrates a schematic perspective view of a preferred embodiment of the endoscopic instrument.

FIG. 1 shows a preferred embodiment of an endoscopic instrument 10. The endoscopic instrument 10, which is embodied as an endoscope, comprises a shaft 12, which has a distal end 14 at which at least one optical sensor 16 is arranged, and a proximal end 18 for connection to a supply unit 20. Between the at least one optical sensor 16 and the proximal end 18 a data transmission element is arranged. The data transmission element is configured to transmit at least two signals differentially. The data transmission element is configured as a star quad cable 22. In a further embodiment (not shown), the star quad cable 22 continues over the proximal end 18 to the supply unit 20. Further, an optical unit 19 may be associated with the optical sensor 16, the optical unit 19 being releasably attached distally, i.e. in the optical path, before the optical sensor 16. Therefore, the optical sensor 16 may or may not be arranged at the very distal end of the endoscopic instrument 10.

Figure 2:
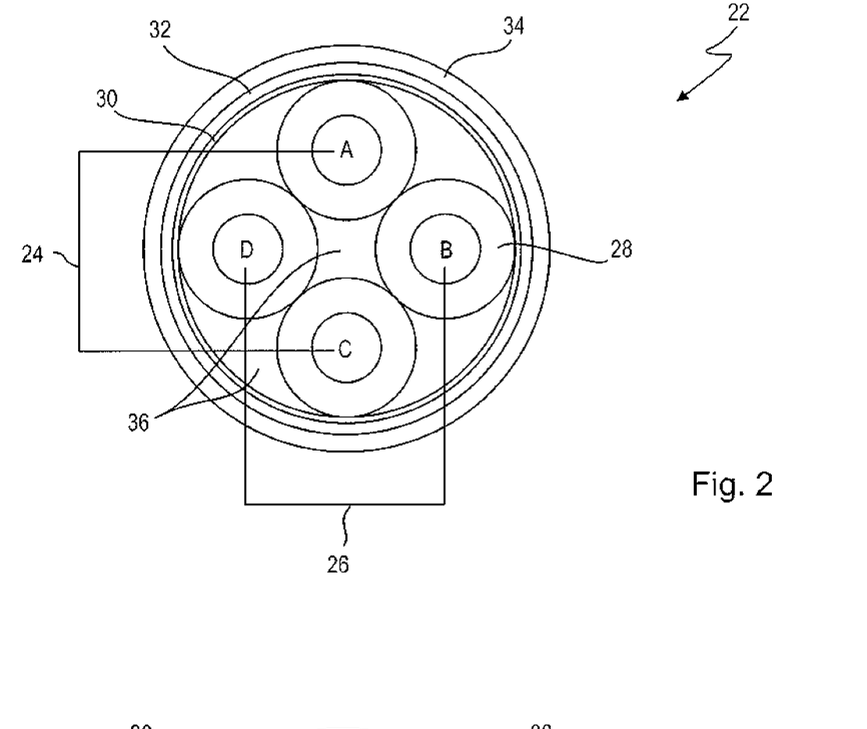
FIG. 2 illustrates a cross-section view according to a first preferred embodiment of the data transmission element.

FIG. 2 shows a schematic cross section of a preferred embodiment of the data transmission element which is embodied as a star quad cable 22.

The star quad cable 22 comprises a first pair of strands 24 and a second pair of strands 26. The first pair of strands 24 comprises strands A and C, the second pair of strands 26 comprises strands B and D. Strands A and C are in opposition to each other and strands B and D are in opposition to each other.

Strands A to D are each surrounded by an insulation 28 and are contained in a sheath which, for this embodiment, has three layers. Both pairs of strands 24, 26 are surrounded by a plastic layer 30. A shielding 32 surrounds the plastic layer 30. The shielding 32 is surrounded by a cover 34 of the star quad cable 22.

The star quad cable 22 has clearances 36 between the individual strands A to D.

Figure 3:
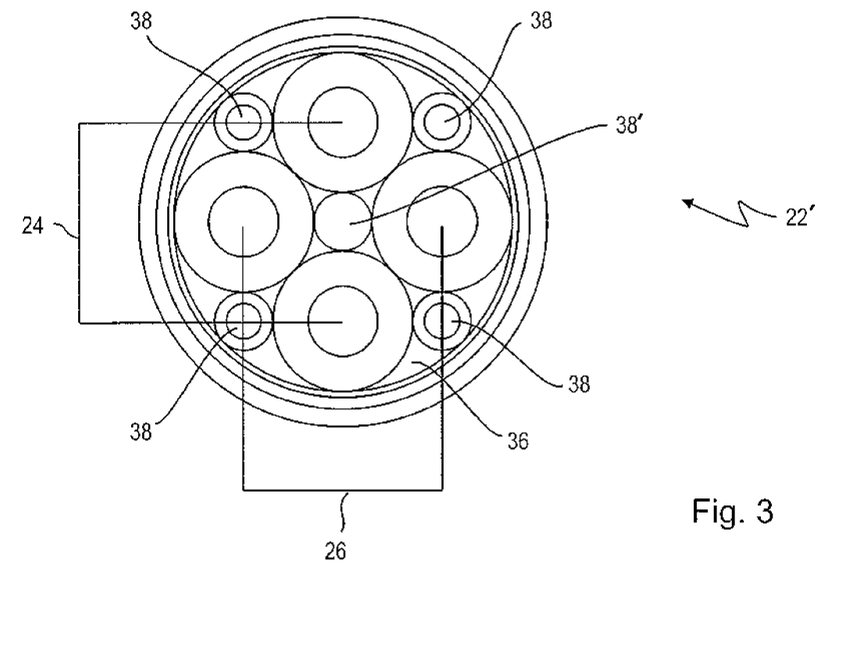
FIG. 3 illustrates a cross-section view according to a second preferred embodiment of the data transmission element.

FIG. 3 shows a second preferred embodiment of a star quad cable 22'. This embodiment comprises pairs of strands 24, 26 as well. In the clearances 36, however, additional strands 38, 38' (wires or fibers) are arranged which may transmit control signals or may provide for the power supply of the optical sensor 16. The additional strands 38, 38' may also be embodied as optical fibers. As shown in the figure, the additional strands 38, 38' are received in the star quad cable 22' without an increase of the outer diameter of the star quad cable 22' in comparison to the embodiment 22 shown in FIG. 2. It may be preferred to provide a ground wire 38' as an additional strand 38 in a clearance 36.

Figure 4:
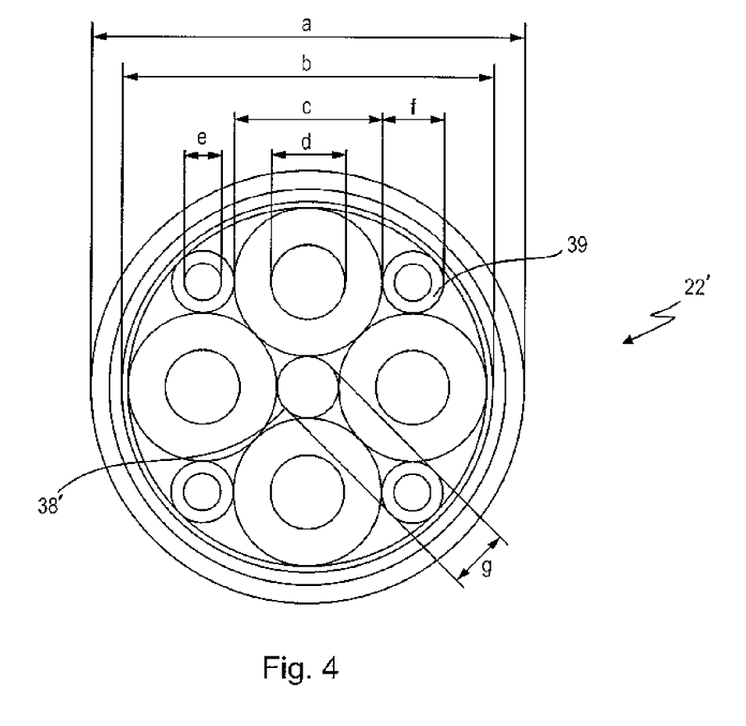
FIG. 4 illustrates the data transmission element according to FIG. 3 with dimensions.

FIG. 4 shows a view of the star quad cable 22' of FIG. 3 with dimensions.

An outer diameter a is preferably less than 5 mm (approx. 0.2 in), more preferred less than 4 mm (approx. 0.16 in) and even more preferred less than 3 mm (approx. 0.12 in). In the shown embodiment of the star quad cable 22', the outer diameter a is 2.5 mm (approx. 0.1 in). The diameter b which represents the outer diameter of the plastic layer 30, is 2.1 mm (approx. 0.08 in).

The outer diameter of the insulation of each strand A to D is shown as c and is in this embodiment 0.8 mm (approx. 0.03 in). The outer diameter of each strand A to D is 0.4 mm (approx. 0.016 in) and is shown as d.

The outer diameter of each additional strand 38 is shown as e and is 0.2 mm (approx. 0.008 in). Also, each additional strand 38 has preferably its own insulation 39 which outer diameter is shown as f and which is 0.3 mm (approx. 0.012 in) for this embodiment.

Also, an outer diameter of a centrally arranged additional strand 38', which is provided as a ground strand in this embodiment, is 0.3 mm (approx. 0.012 in) and is shown as g.

Using the shown star quad cable 22' allows to achieve good electrical characteristics for the application in the endoscopic instrument 10. The differential characteristic wave impedance of a pair of strands is preferably at 100Ω. The attenuation at 400 MHz is less than 1.0 dB/m, in particular 0.8 dB/In or less.

The DC resistance of the strands A to D may be less than 0.5 Ω/m, in particular 0.2 Ω/m or less. The DC resistance in the additional strands 38 may be less than 1.0 Ω/m, in particular 0.58 Ω/m or less. The DC resistance of the additional strand 38' which is embodied as a ground wire may be less than 0.5 Ω/m, in particular 0.39 Ω/m or less.

To achieve the required insulation 38, 39 a material is preferably chosen so that the insulation resistance is at least 1500 MΩkm. The test voltage is 500V.

Figure 5:
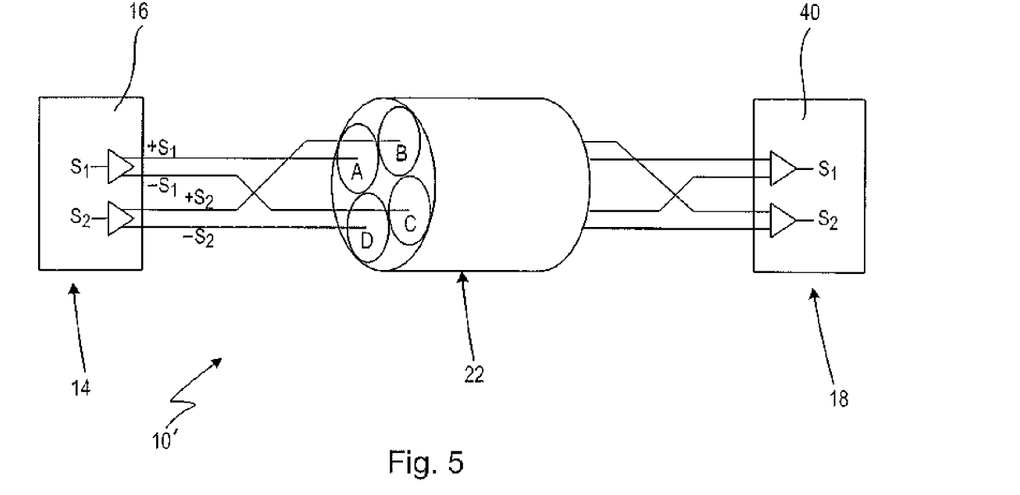
FIG. 5 illustrates a preferred embodiment of a connecting arrangement of an endoscopic instrument.

FIG. 5 shows a schematic connection scheme of a preferred embodiment 10' of an endoscopic instrument.

The connecting arrangement of FIG. 5 is provided in order to differentially transmit two signals s1 (+s1/−s1) and s2 (+s2/−s2) between the optical sensor 16 and a proximal end 18.

The endoscopic instrument 10' is connected at the proximal end 18 to a control unit 40 with amplifier, which receives signals s1 and s2 and supplies them to the supply unit 20 (not shown).

The differential signal +s1/−s1 is transmitted via the first pair of strands 24 by, e.g., transmitting a signal portion +s1 to strand A and a signal portion −s1 to strand C.

The second differential signal +s2/−s2 is transmitted via the second pair of strands 26 by, e.g., sending a signal portion +s2 to strand B and a signal portion −s2 to strand D. Due to the given symmetry the opposite fields caused by the strands A and C cancel each other at the positions of the strands B and D, and vice versa. Therefore, there is little or no influence between both signals s1 and s2, meaning, there is little or no cross talk between the first pair of strands 24 and the second pair of strands 26.

The shown connecting arrangement is suitable for a transmission using the MIPI CSI-2 "one lane" standard.

Figure 6:
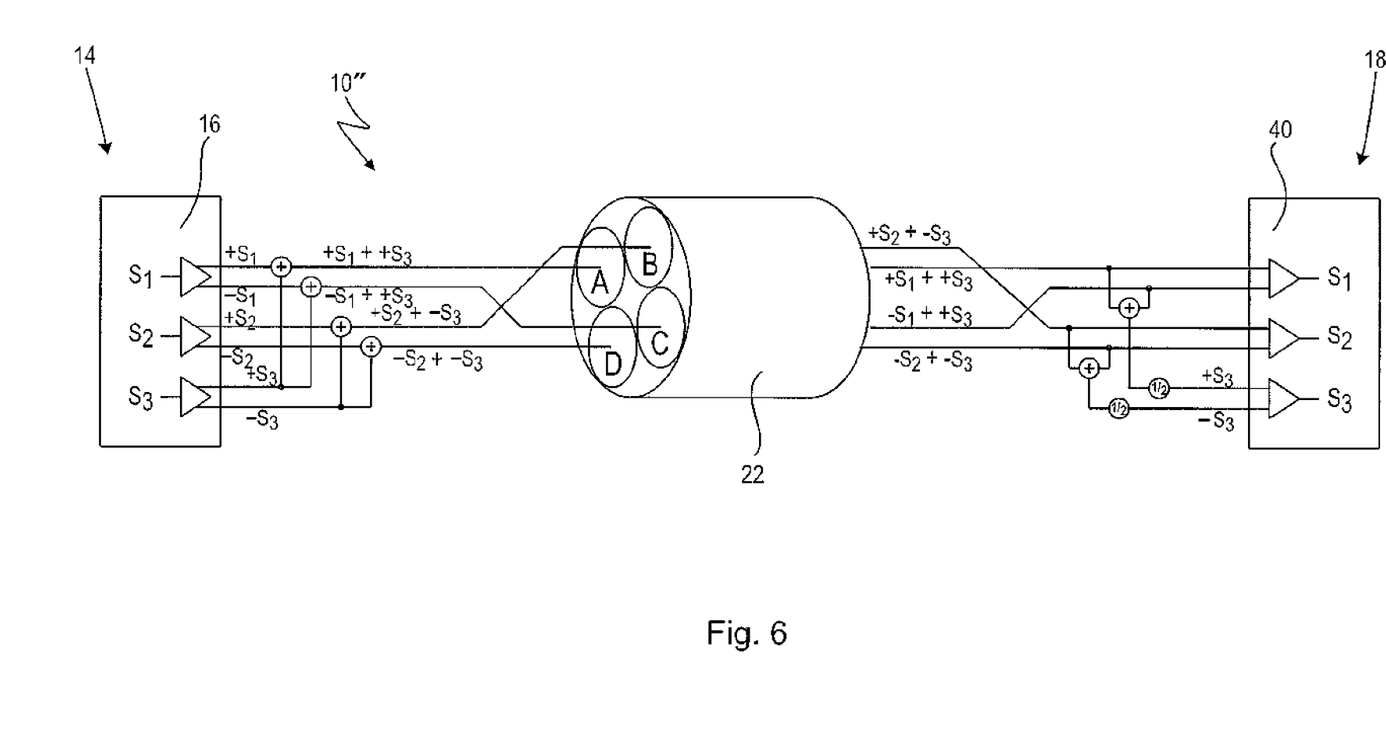
FIG. 6 illustrates a further preferred embodiment of a connecting arrangement of an endoscopic instrument.

FIG. 6 shows a preferred embodiment 10" of an endoscopic instrument with a connecting arrangement between the optical sensor 16 and the proximal end 18 which is suitable to transmit three signals s1, s2, s3 via the star quad cable 22. The transmission of the first differential signal +s1/−s1 and the second differential signal +s2/−s2 is achieved with a connecting arrangement as shown in FIG. 5.

In addition, a third differential signal +s3/−s3 is transmitted over the pairs of strands 24 and 26. For example, a first signal portion +s3 is added to the signals of strands A and C, while a signal portion −s3 is added to the signals of strands B and D. For symmetry reasons the fields produced by the signal portions +s3 and −s3 at the positions of strands A and C are the same as well as at the positions of the strands B and D. This means that there is little or no influence of the differential signals in the first pair of strands 24 and the second pair of strands 26 caused by the third differential signal +s3/−s3.

The recovery of the third differential signal +s3/−s3 is achieved by adding the signals of strands A and C at the proximal end 18 on top. When adding, the signal portions +s1 and −s1 cancel each other, so that a signal portion results which is double of +s3. Dividing the signal by 2 recovers the signal portion +s3. In the same manner, the signal portion −s3 can be recovered by adding the signals of strands B and D and a subsequent division by 2, since the signal portions +s2 and −s2 cancel each other when adding.

The connecting arrangement is suitable for the MIPI CSI-2 "two lane" standard. For example, an image data signal is distributed onto two channels or two signals. This results, while maintaining the same image resolution, in a reduced demand regarding the transmission bandwidth per signal, so that longer distances can be achieved at the same signal quality.

Further, this embodiment allows to transmit two different image data signals (s1 and s2) and to transmit, at the same time, a clock signal (s3) from the proximal end 18 to the distal end 14.

Further, this embodiment allows to arrange two optical sensors at the distal end in a stereoscopic arrangement.

Figure 7:
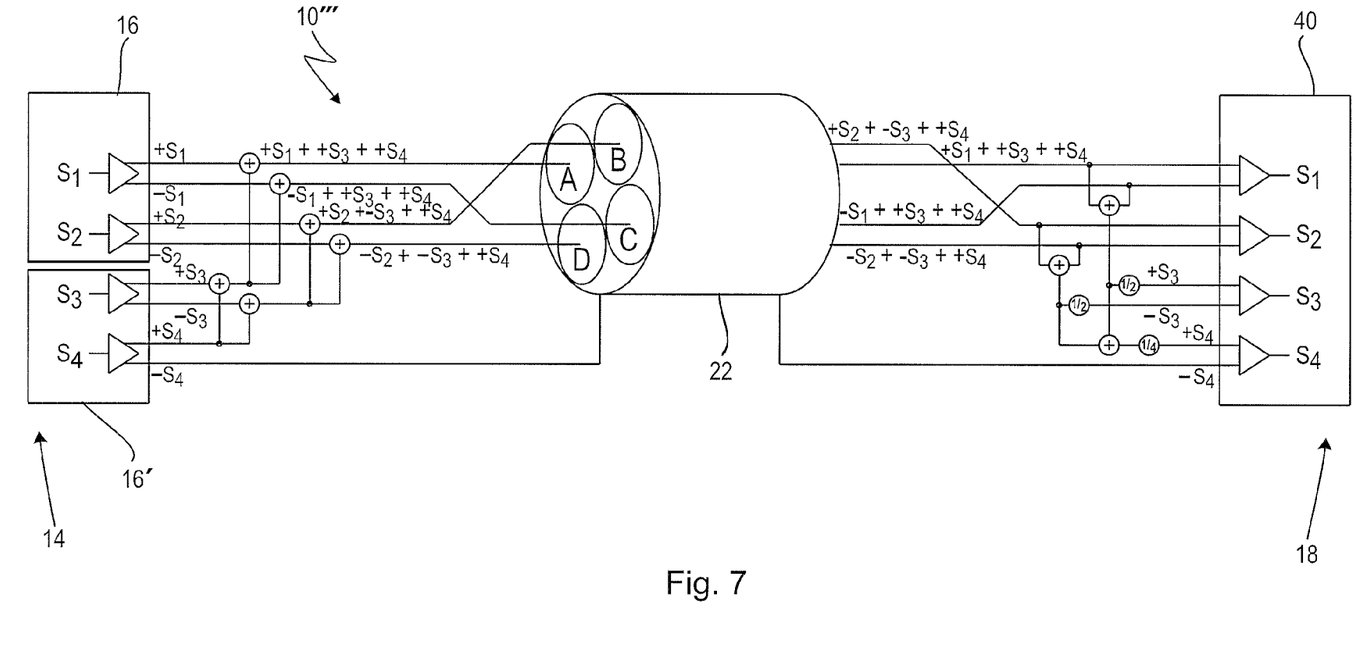
FIG. 7 illustrates yet a further preferred embodiment of a connecting arrangement of an endoscopic instrument.

FIG. 7 shows a further preferred embodiment 10" of an endoscopic instrument with a connecting arrangement that is suitable to differentially transmit four signals s1 to s4.

The connecting arrangement for transmitting the first three signals s1 to s3 corresponds to the arrangement shown in FIG. 6.

A fourth differential signal +s4/−s4 is transmitted, e.g., by adding a signal portion +s4 to all strands A to D, while a signal portion −s4 is applied to the shielding of the star quad cable 22'. Due to the differential transmission the other three signals s1 to s3 are not influenced by the fourth signal s4.

The recovery of the fourth signal s1 at the control unit 40 at the proximal end 18 is preferably achieved by adding the signal portions of strands A to D, and then dividing the resulting signal by 4. The signal portions +s1/−s1, +s2/−s2, +s3/−s3 cancel each other so that a summing signal of four times +s4 is obtained, which, when divided by 4, results in the signal portion +s4. The signal portion −s4 is obtained directly from the shielding, so that the control unit 40 can determine the signal s4.

In a further preferred embodiment, not shown, three signals s1, s2 and s4 are transmitted differentially. This means, a third signal does not have to be transmitted via the connecting arrangement shown in FIG. 6, but can also be transmitted via the shown connecting arrangement of FIG. 7 for the signal s4. Therefore, the connecting arrangement shown in FIG. 7 for signal s4 is available also without a transmission of a signal s3. It is sufficient to apply a signal portion +s4 to all strands A to D and to apply the signal portion −s4 to the shielding.

Using the four signals s1 to s4, two optical sensors 16 and 16' can be used simultaneously and independently from one another, each using the MIPI CSI-2 "one lane" standard. This arrangement is suitable for, e.g., stereoscopic applications with two optical sensors 16, 16' at the distal end. Further, other arrangements with two optical sensors for different fields of view or different spectral sensitivities, e.g. in fluorescence applications, are possible.

It is understood that the optical sensors 16 and 16' may be single frame sensors, e.g. used for taking photos, but may also be sensors for constant recording, as in video applications.

Figure 8:
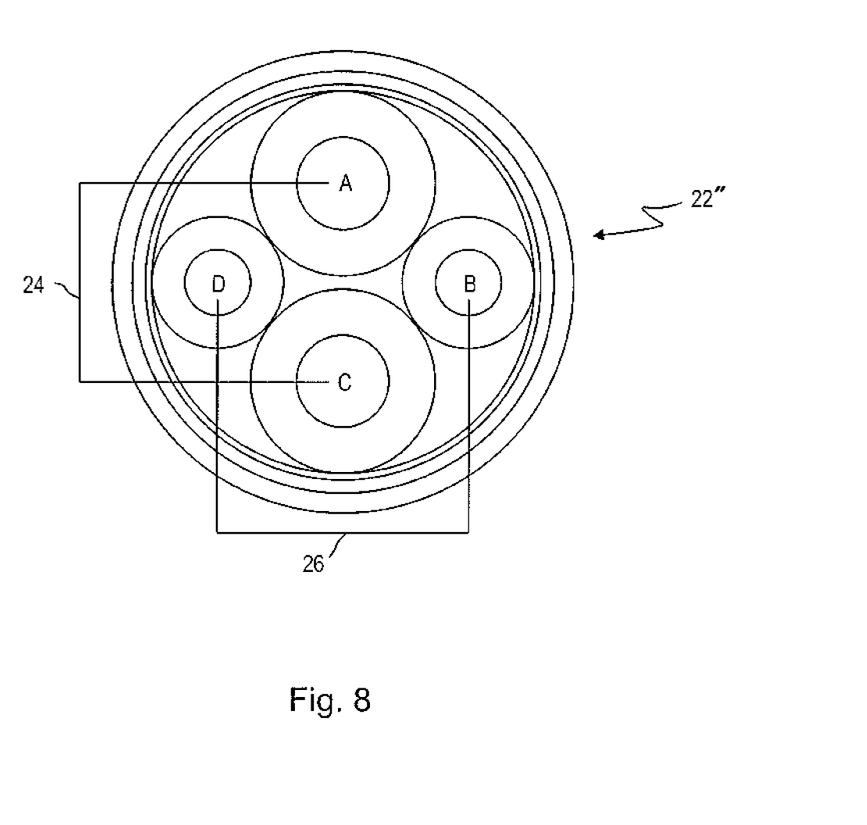
FIG. 8 illustrates a cross section view of yet a further preferred embodiment of a data transmission element.

FIG. 8 shows a further preferred embodiment of the star quad cable 22". A first differential signal s1 which is transmitted via the first pair of strands 24 is configured for the transmission of image data and a second differential signal s2 which is transmitted via the second pair of strands 26 is configured for the transmission of a clock signal. For exemplary purposes only two signals are shown, however, the following preferred embodiments can also be used with three of four signals.

The outer diameter of the first pair of strands 24, however, has a different diameter than the second pair of strands 26. Specifically, the diameters of strands A and C of the first pair of strands 24 is larger than the diameter of the strands B and D of the second pair of strands 26.

This arrangement may be preferable, if a signal that changes periodically between two levels, e.g. the clock signal, and a non-periodic signal, e.g. the image data signal, are transmitted. A greater attenuation can be accepted for the periodic signal, since no deterministic jitter is caused by the attenuation. Therefore, a smaller diameter of the conductor may be chosen for this signal. The physical background of the deterministic jitter is known to the skilled person. At the same time, choosing a smaller diameter, allows for a greater diameter of the other pair of strands while maintaining the outer diameter, the first pair of strands 24 for the example shown in FIG. 8. Therefore, a reduced attenuation can be achieved for the non-periodic signal.

Specifically, when transmitting data according to the MIPI CSI-2 standard, by distinguishing between a clock signal and a data signal an increased attenuation of the clock signal may be accepted in return for a decreased attenuation of the image data signal.

Figure 9:
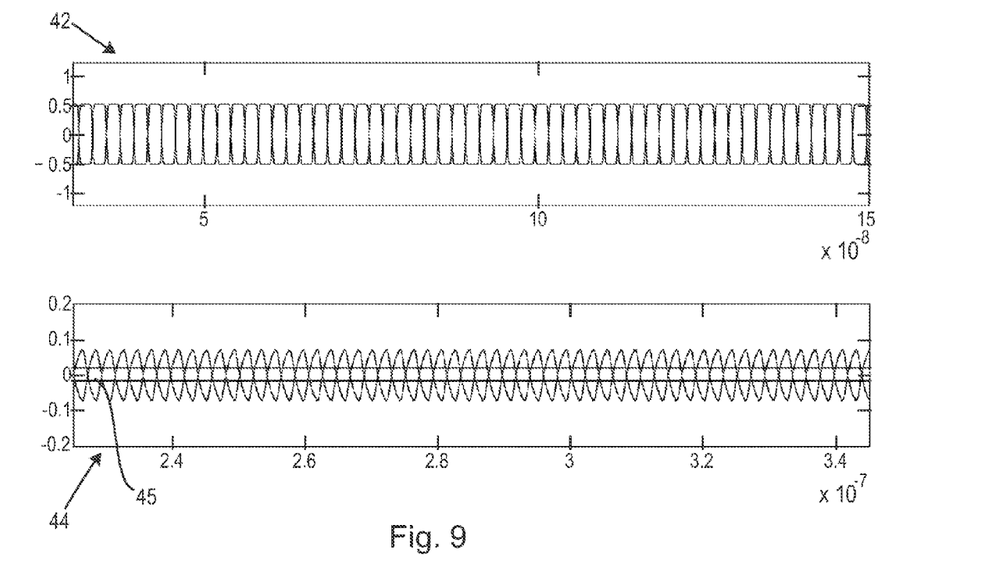
FIG. 9 illustrates the temporal development of an exemplary clock signal.

FIG. 9 shows a differential clock signal when being transmitted via a data transmission element which is embodied as a star quad cable 22, where the first pair of strands 24 and the second pair of strands 26 have the same diameter. The signal sent is shown with reference numeral 42, and a signal received is shown with reference numeral 44. In the signal received 44 a comparator threshold 45 is shown which must be exceeded so that a bit can be detected with certainty by the receiver.

Figure 10:
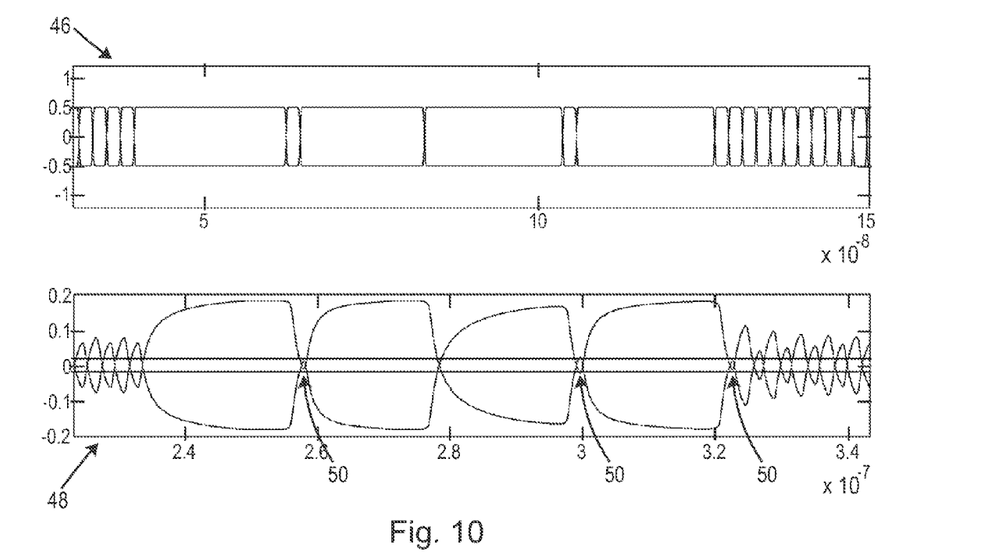
FIG. 10 illustrates an exemplary image signal on a data transmission element.

FIG. 10 shows an image data signal which is simultaneously transmitted with the clock signal of FIG. 9. The image data signal at the sender side is shown with reference numeral 46, the image data signal at the receiver side is shown with reference numeral 48. As is shown, not all bits can be identified correctly.

Those portions of the signal, where the amplitude does not exceed the comparator threshold, such that the corresponding bit cannot be detected correctly, are shown with arrows 50. In particular, long sequences of 0-bits (or 1-bits) which are interrupted by 1-bits (or 0-bits), respectively, may be problematic. The opening windows of the signal received 48 are notably smaller at the faulty locations 50 than in the clock signal 44 at the receiver side as shown in FIG. 9.

For such cases, the preferred embodiment of the star quad cable 22' as shown in FIG. 8 is particularly useful.

Figure 11:
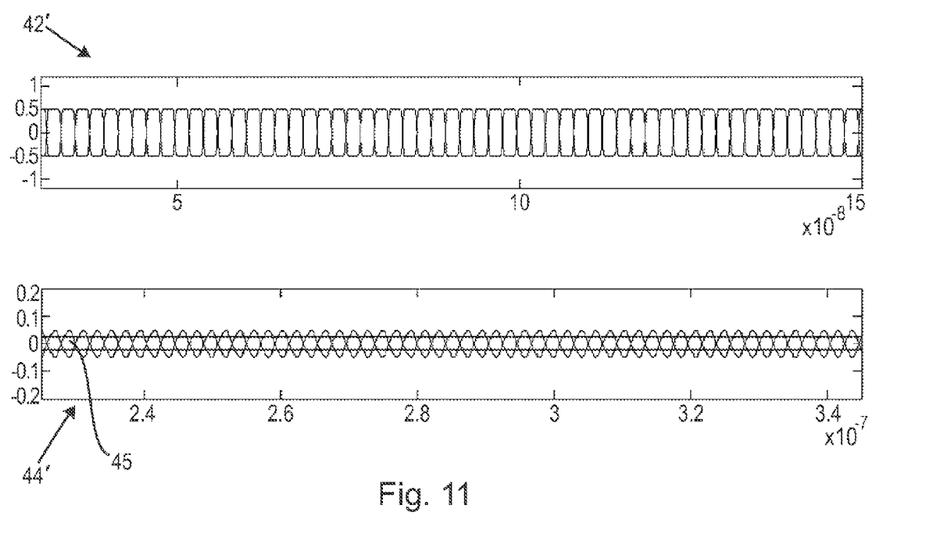
FIG. 11 illustrates an exemplary clock signal when using the data transmission element according to FIG. 8.
Figure 12:
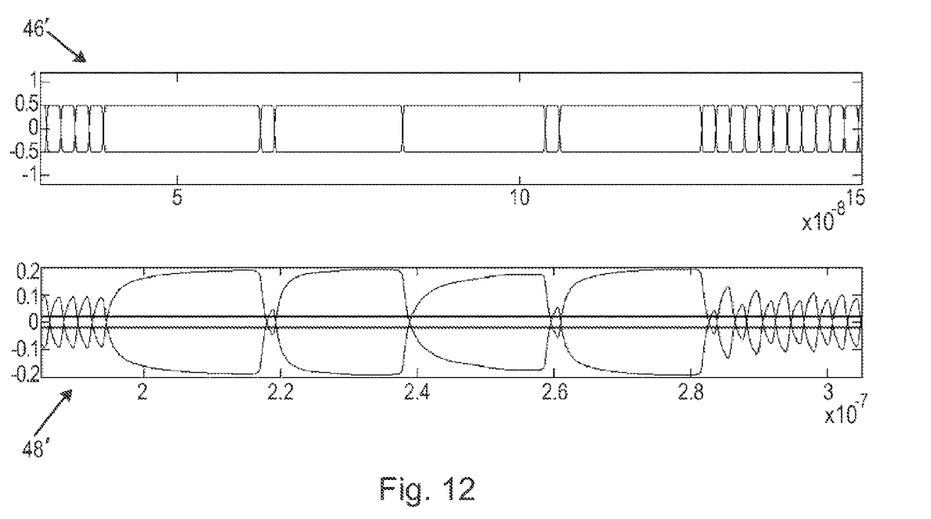
FIG. 12 illustrates an exemplary image signal when using the data transmission element according to FIG. 8.

FIGS. 11 and 12 show a clock signal 42' at the sender side and an image data signal 46' at the sender side as well as a clock signal 44' at the receiver side and an image data signal 48' at the receiver side, respectively.

An outer diameter of the data transmission element is the same as for the signals that are transmitted according to FIGS. 9 and 10. It can be seen that the clock signal 44' at the receiver side may have a smaller amplitude then that of FIG. 9, however, the comparator threshold 45 is always exceeded.

Also, the data signal 48' at the receiver side exceeds the comparator threshold 45. This is achieved by the reduced attenuation of the first pair of strands 24 with a greater diameter as shown in FIG. 8. The opening windows of the clock signal 44' at the receiver side and of the image data signal 48' at the receiver side are now about the same.

Figure 13:
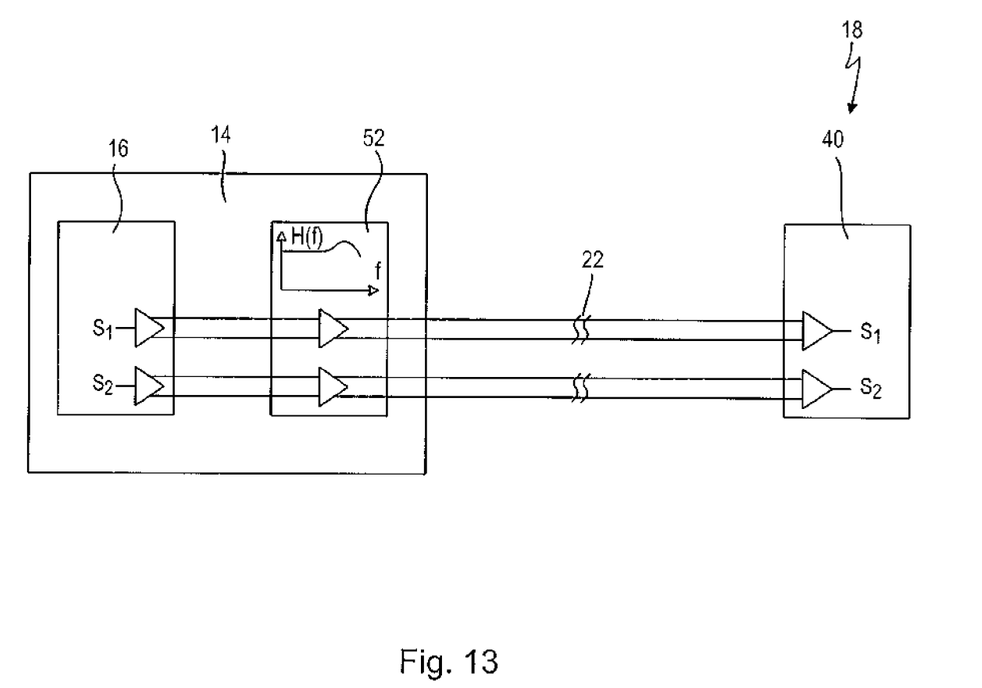
FIG. 13 illustrates a schematic view of yet a further preferred embodiment of an endoscopic instrument.

FIG. 13 shows a further possible embodiment of the endoscopic instrument 10, which may be applied alternatively or in addition to the previously described preferred embodiments of the star quad cable 22, in order to improve the quality of the transmission of signals s1 to s4.

To do so, a driving unit 52 is provided at the distal end 14, where a pre-distortion with pre-emphasis is applied at the sender side.

Figures 14, 15:
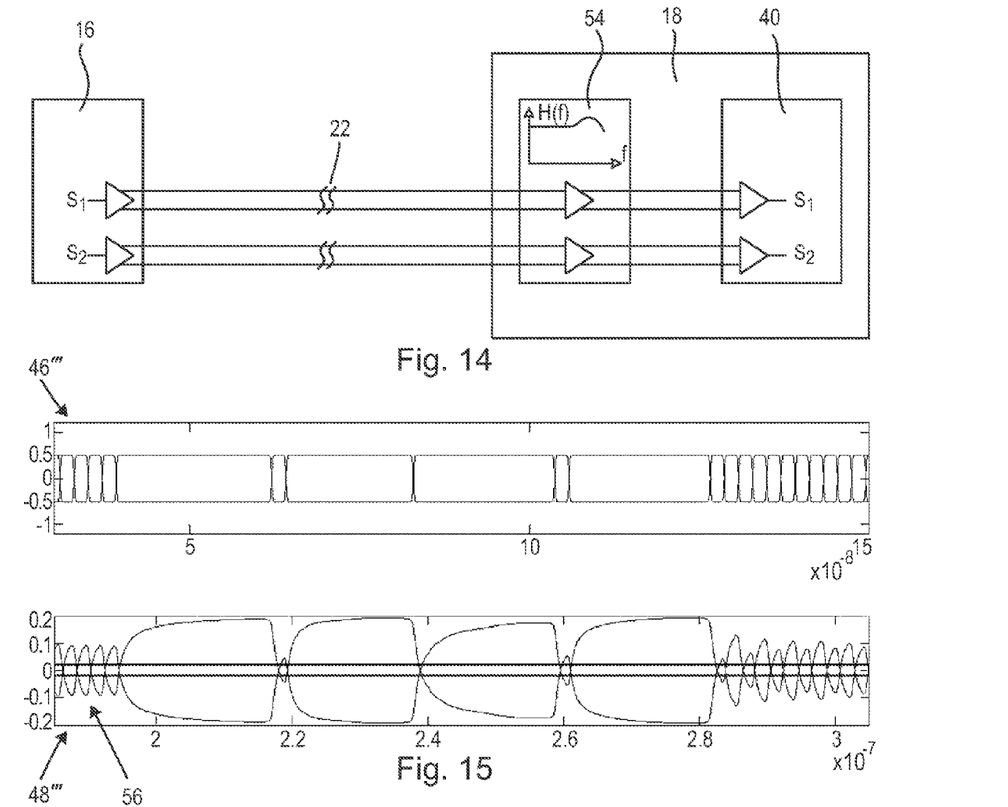
FIG. 14 illustrates a schematic view of yet a further preferred embodiment of an endoscopic instrument.
FIG. 15 illustrates an image signal when using the embodiment according to FIG. 14 and when omitting an equalization unit.

FIG. 14 shows that alternatively an equalization using the equalization unit 54 can be provided at the receiver side at the proximal end 18. The equalization at the receiver side can also be provided in addition to the pre-distortion.

The pre-distortion at the sender side or the equalization at the receiver side leads to an increase in the high-frequency spectral components, in order to compensate for the attenuation characteristics of the star quad cable 22 (namely, an increasing attenuation as the frequency increases). This allows for a significant increase of the star quad cable 22 while maintaining the same outer diameter.

Figure 16:
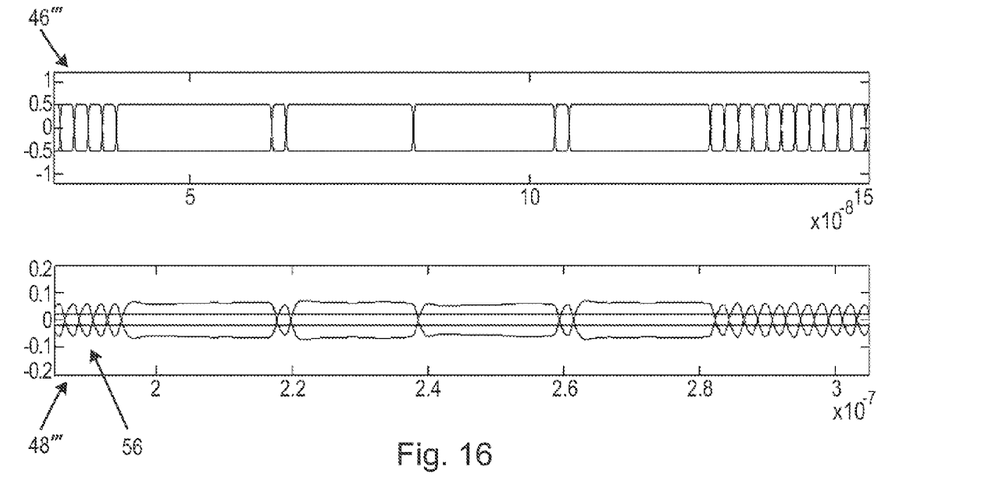
FIG. 16 illustrates an image signal when using the embodiment according to FIG. 14 and when using an equalization unit.

The effects on the signals at the receiver side are shown in FIGS. 15 and 16.

FIG. 15 shows the temporal development of an image data signal 46" at the center side and of an image data signal 48" at the receiver side without equalization.

FIG. 16 shows the temporal development of an image data signal 46''' at the center side and of an image data signal 48''' at the receiver side having the same arrangement, however, using an equalization unit 54.

A maximum amplitude of the signal 48''' at the receiver side is significantly reduced in comparison to a maximum amplitude of the signal 48" at the receiver side. However, the maximum amplitude of single bits 56 is significantly increased. This results in an increase of the opening windows for these single bits 56, so that a reliable detection of the single bits is possible.

The quality of the transmission may thus be further increased.

What is claimed is:

1. An endoscopic instrument comprising a shaft having a distal end at which at least one optical sensor is arranged and a proximal end configured for a connection to a supply unit, further comprising a data transmission element which is provided between said at least one optical sensor and said proximal end and which is configured to differentially transmit at least two signals,
wherein said data transmission element is embodied as a star quad cable, said star quad cable includes at least a first pair of strands having two strands in opposition to each other and a second pair of strands having two further strands in opposition to each other, and further includes at least one clearance between said first pair of strands and said second pair of strands, wherein at least one additional strand is arranged in said at least one clearance.

2. The endoscopic instrument according to claim 1, wherein said at least one optical sensor is connected to said star quad cable such that at least three signals can be differentially transmitted.

3. The endoscopic instrument according to claim 1, wherein said at least one optical sensor is connected to said star quad cable such that at least four signals can be differentially transmitted.

4. The endoscopic instrument according to claim 3, wherein a first signal and a second signal of said at least two signals are an image data signal and a clock signal of a first of said at least one optical sensor, and wherein a third signal and a fourth signal of said at least two signals are configured as an image data signal and a clock signal of a second of said at least one optical sensor.

5. The endoscopic instrument according to claim 1, wherein said star quad cable comprises at least a first pair of strands having two strands in opposition to each other and a second pair of strands having two further strands in opposition to each other, wherein a diameter of said strands of said first pair of strands is different from a further diameter of said strands of said second pair of strands.

6. The endoscopic instrument according to claim 1, wherein said at least one additional strand is configured for supplying power to said at least one optical sensor.

7. The endoscopic instrument according to claim 1, wherein said at least one additional strand is configured for controlling said at least one optical sensor.

8. The endoscopic instrument according to claim 1, wherein said at least one additional strand is configured as an optical fiber.

9. The endoscopic instrument according to claim 1, wherein a first signal of said at least two signals is configured as an image data signal and a second signal of said at least two signals is configured as a clock signal.

10. The endoscopic instrument according to claim 9, wherein a transmission of image data is based on a MIPI CSI-2 standard.

11. The endoscopic instrument according to claim 1, wherein a driving unit with amplification is arranged at said distal end for pre-distorting image data of said at least one optical sensor.

12. The endoscopic instrument according to claim 1, wherein an equalization unit is arranged at said proximal end for equalizing image data of said at least one optical sensor.

13. The endoscopic instrument according to claim 1, wherein said star quad cable has a diameter of less than 5 mm and a length of at least 0.5 m.

14. The endoscopic instrument according to claim 1, further comprising an optical unit that is associated with said at least one optical sensor and which is arranged at a distal side before said at least one optical sensor and which is provided with a coupling which is at least partially releasable.

15. The endoscopic instrument according to claim 1, wherein said at least one optical sensor comprises a digital interface according to an MIPI CSI-2 standard.

16. An endoscopic instrument comprising a shaft having a distal end at which at least one optical sensor is arranged and a proximal end configured for a connection to a supply unit, further comprising a data transmission element which is provided between said at least one optical sensor and said proximal end and which is configured to differentially transmit at least two signals, wherein said data transmission element is embodied as a star quad cable and said at least one optical sensor is connected to said star quad cable such that at least three signals can be differentially transmitted.

17. The endoscopic instrument according to claim 16, wherein said star quad cable comprises at least a first pair of strands having two strands in opposition to each other and a second pair of strands having two further strands in opposition to each other, and further comprising at least one clearance between said first pair of strands and said second pair of strands, wherein at least one additional strand is arranged in said at least one clearance;

wherein said at least one additional strand is configured for at least one of supplying power to said at least one optical sensor or controlling said at least one optical sensor.

18. An endoscopic instrument comprising a shaft having a distal end at which at least one optical sensor is arranged and a proximal end configured for a connection to a supply unit, further comprising a data transmission element which is provided between said at least one optical sensor and said proximal end and which is configured to differentially transmit at least two signals, wherein said data transmission element is embodied as a star quad cable; and wherein a first signal of said at least two signals is configured as an image data signal and a second signal of said at least two signals is configured as a clock signal.

19. The endoscopic instrument according to claim 18, wherein said star quad cable comprises at least a first pair of strands having two strands in opposition to each other and a second pair of strands having two further strands in opposition to each other, and further comprising at least one clearance between said first pair of strands and said second pair of strands, wherein at least one additional strand is arranged in said at least one clearance; and wherein said at least one additional strand is configured as an optical fiber.

* * * * *